United States Patent [19]

Ganguly et al.

[11] 4,076,711

[45] Feb. 28, 1978

[54] TRIAZOLO [4,5-d]-PYRIMIDINES

[75] Inventors: Ashit K. Ganguly, Upper Montclair, N.J.; Edwin A. Peets, New York, N.Y.; Anil K. Saksena, Upper Montclair, N.J.

[73] Assignee: Schering Corporation, Kenilworth, N.J.

[21] Appl. No.: 753,205

[22] Filed: Dec. 22, 1976

Related U.S. Application Data

[63] Continuation-in-part of Ser. No. 673,785, Apr. 5, 1976, abandoned.

[51] Int. Cl.² ..................... A61K 31/41; C07D 487/04
[52] U.S. Cl. ..................... 260/256.4 F; 260/256.4 C; 260/256.4 N; 424/251
[58] Field of Search .................................. 260/256.4 F

[56] References Cited

U.S. PATENT DOCUMENTS 2,407,204  9/1946  English et al. ................ 260/256.4 F

*Primary Examiner*—Donald G. Daus
*Assistant Examiner*—James H. Turnipseed
*Attorney, Agent, or Firm*—Stephen B. Coan; Raymond A. McDonald; Bruce M. Eisen

[57] ABSTRACT

This disclosure relates to the method for the treatment of psoriasis which comprises the topical administration to a mammal suffering from psoriasis of an effective dose for treating psoriasis of a 7X-5Q-3Y-3H-γ-triazolo[4,5-d]-pyrimidine wherein X is halogeno, alkoxy, or —NRR$_1$, R and R$_1$ being lower alkyl, Y is cycloalkyl, hydroxycycloalkyl, phenyl, bicycloalkyl, or A—R$_2$ with A being methylene or ethylene and R$_2$ being phenyl or bicycloalkyl, and Q is hydrogen or Y.

6 Claims, No Drawings

TRIAZOLO [4,5-D]-PYRIMIDINES

This application is a continuation-in-part application of our copending Application Ser. No. 673,785, filed Apr. 5, 1976 now abandoned.

This invention relates to the use of certain purines in the treatment of psoriasis. More particularly, this invention relates to the treatment of psoriasis in mammals which comprises the administration to a mammal suffering from psoriasis of an effective dose for treating psoriasis of a compound of the structural formula:

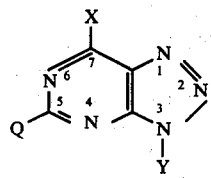

wherein X is selected from the group consisting of halogeno, $-NR_1R$, and lower alkoxy, with R and $R_1$ each being hydrogen or lower alkyl; Y is selected from the group consisting of lower alkyl, cycloalkyl, hydroxy cycloalkyl, phenyl, bicycloalkyl, or $A-R_2$ with A being methylene or ethylene and $R_2$ being phenyl or bicycloalkyl, and Q is hydrogen or Y, said aromatic substituents optionally being substituted with halogeno or trifluoromethyl.

When used, the term lower alkyl includes those straight and branched-chained saturated lower aliphatic hydrocarbyl radicals having from one to six carbon atoms exemplified by such radicals as methyl, ethyl, t-butyl, isopropyl, amyl, isoamyl and the like; the term lower cycloalkyl includes those cyclized saturated hydrocarbyls having from 3 to 10 carbon atoms preferably embracing cyclobutyl, cyclopentyl, cyclohexyl and cycloheptyl. Halogeno preferably includes chloro, bromo and iodo. Preferred $NRR_1$ radicals are dimethylamino and diethylamino. Bicycloalkyl radicals include those radicals having up to 12 carbon atoms, (optionally substituted with a hydroxyl radical) and include such a preferred radical as exo-2-norbonyl. Preferred $A-R_2$ radicals are benzyl, phenethyl, and cis- or trans myrtanyl. Preferred lower alkoxy radicals are methoxy and ethoxy although those radicals having up to six carbon atoms are embraced herein.

In those instances wherein Y represents a substituted aromatic group, it is preferred that the halogen or the trifluoromethyl be located in the para position of the phenyl, benzyl or phenethyl substituent, whilst those saturated hydrocarbyl radicals bearing a hydroxy substituent preferably have such substituent at the ortho position.

Psoriasis is a common, chronic, relapsing disease of unknown etiology which consists of elevated, silvery, dry lesions commonly known as plaques. Pathologically there are three obvious changes associated with the disease: (1) increase in the rate of cell division of the epidermis, (2) striking difference in the thickness of the cornified epithelium and (3) proliferation of the subepithelial capillaries. In human psoriasis, when the involved hyperplastic epidermis is compared to uninvolved epidermis of the same individual, cyclic 3',5'-guanosine monophosphate (cyclic GMP or cGMP) levels are found to be greatly elevated while at the same time there is a decrease in cyclic 3,5-adenosine-monophosphate (cyclic AMP or cAMP) levels. This factor is consistent with evidence from a variety of systems supporting the view that a temporally discrete rise in cellular cGMP concentration is the active signal to induce proliferation while increased cyclic AMP levels tend subsequently to limit or inhibit this mitotic action. Thus, an inhibition of the intracellular enzyme responsible for hydrolyzing cAMP, i.e. cyclic AMP phosphodiesterase, would tend to correct the imbalance and the resultant higher cAMP levels would exert an antiproliferative effect on the epidermis. This contention is supported by the demonstration that papaverine, a phosphodiesterase inhibitor was clinically effective in treating human psoriasis.

Utilizing standard assay techniques, the compounds of this invention (I) have been found to possess (a) phosphodiesterase inhibitory activity, (b) in vivo activity blocking retinoic acid stimulated protein and DNA synthesis with concomitant effects on histological changes in the guinea pig epidermis and (c) inhibits the croton-oil stimulated mitosis in the mouse epidermis. With such techniques, as well as by comparison with known anti-psoriasis agents, it is found that the compounds of this invention are useful in the treatment of psoriasis by the topical administration of 0.1 mgm. to 5.0 mgm. of active ingredient per lesion per day.

As is true for most classes of compounds which have been found to be therapeutically useful, certain members of the generic class are found to be more efficient than others. On the basis of the assay techniques, it is found that those compounds having a halogeno substituent, (preferably chloro) in the 7-position of the 3H-γ-triazolo [4,5-d]-pyrimidine molecule are particularly effective, as well as those compounds having a cyclohexyl, isoamyl, or a cyclopentyl substituent in the 3-position of the 3H-γ-triazolo [4,5-d]-pyrimidine molecule. Particularly affective compounds of this invention are 7-chloro-3-cyclohexyl 3H-γ-triazolo [4,5-d]-pyrimidine, 7-chloro-3-cyclopentyl 3H-γ-triazolo [4,5-d]-pyrimidine, 7-chloro-3-cycloheptyl 3H-γ-triazolo [4,5-d]-pyrimidine, 7-chloro-3-isoamyl 3H-γ-triazolo [4,5-d]-pyrimidine, and 7-methoxy-3-cyclopentyl-3H-γ-triazolo [4,5-d]-pyrimidine. A group of novel compounds worthy of being grouped together are 7-chloro-3-cyclohexyl-3H-γ-triazolo[4,5-d]pyrimidine, 7-chloro-3-cycloheptyl-3H-γ-triazolo[4,5-d]-pyrimidine, 7-chloro-3-cyclobutyl-3H-γ-triazolo[4,5-d]-pyrimidine, 7-iodo-3-cyclohexyl-3H-γ-triazolo[4,5-d]-pyrimidine, and 7-methoxy-3-cyclopentyl-3H-γ-triazolo[4,5-d]-pyrimidine.

In carrying out the method for treating psoriasis, the active ingredient (i.e. those compounds of formula I) is formulated into a topical preparation and applied to a psoriatic lesion at a rate varying from 0.1 mg. cm² of skin surface per day to about 10 mg. cm² of skin per day until the appearance of the psoriatic skin has returned to normal. In the topical formulations the active ingredient can vary from about 0.1% to about 5% by weight.

The following are the examples illustrating the pharmaceutical formulations and preparations of the compounds of this invention. The desired concentrations range from 0.1% to 2%.

A. Ointment

| Formula | mg./g. |
|---|---|
| 7-Chloro-3-Cyclohexyl 3H-γ-triazolol [4,5-d]-pyrimidine, Micronized | 1-20.0 |
| Mineral Oil, U.S.P. | 50.0 |

-continued

| Formula | mg./g. |
|---|---|
| White Petrolatum, U.S.P. to make | 1.0 g |

PROCEDURE

A weighed quantity of white petrolatum, mineral oil, are heated to 65° C and uniformly mixed. The mixture is cooled to 50°–55° C with stirring. The 7-chloro-3-cyclohexyl 3H-γ-triazolo [4,5-d]-pyrimidine, which has been dispersed in a portion of the mineral oil and milled, is added to the above with stirring. The ointment is cooled to RT.

B. Lotion

| Formula | mg./g. |
|---|---|
| 7-Chloro-3-cyclopentyl 3H-γ-triazolo [4,5-d]-pyrmidine, Micronized | 1–20.0 |
| Aluminum Monostearate | 50.0 |
| Isopropyl Myristate to make | 1.0 g. |

PROCEDURE

Heat about 90% of required isopropyl myristate to 60° C. Add aluminum monostearate. Dissolve 7-chloro-3-cyclopentyl 3H-γ-triazolo [4,5-d]-pyrimidine in the remaining quantity of isopropyl myristate. Add with stirring the solution of 7-chloro-3-cyclopentyl 3H-γ-triazolo [4,5-d]-pyrimidine to the thickened solution of aluminum monostearate in isopropyl myristate previously cooled to 45° C. The lotion is cooled to room temperature with agitation.

C. Gel

| Formula | mg./g. |
|---|---|
| 7-Chloro-3-Isoamyl 3H-γ-triazolo [4,5-d]-pyrimidine, Micronized | 1–20.0 |
| Polyethylene and Copolymers (A-C8) | 100.0 |
| Mineral Oil, Light to make | 1.0 g. |

PROCEDURE

Add a portion of mineral oil (about 90%) in a suitable vessel. Heat to about 80° C. Add polyethylene (A-C8) to the mineral oil. The mixture is agitated slowly while hot until all the polyethylene is dissolved. Cool the above mixture quickly by placing the vessel in a cooling bath of 10°–15° C and resume the agitation at normal speed. Once the content of the vessel has reached approximately 45° C, add a solution of 7-chloro-3-isoamyl 3H-γ-triazolo [4,5-d]-pyrimidine, which was dissolved in the remaining mineral oil at 45° C, to the above polymer solution. Allow the mixture to air cool with slow agitation. This will result in a gel form.

The novel compounds of this invention may be prepared by methods analogously known in the art, including references such as the review article by J. Gut in Advances in Heterocyclic Chemistry, Vol. 1, p. 189 (1963), and such others as P. K. Chang et al., J. Med. Chem., 11, 513 (1968), S. Gabriel, et al., Ber. Deut. Chem. GES, 34, 1234 (1901), R. O. Roblin, et al., JACS, 67, 290 (1945), G. M. Timmis, et al., Chem. Abs., 51, 10531 (1957), and H. Erlemeyer, et al., Helv. Chem. Acta., 34, 835 (1951).

In brief, the compounds of this invention may be prepared from 2-Q-5-amino-4,6-dichloropyrimidine (II) which, when reacted with the appropriately Y-substituted amine, produces the corresponding 2-Q-6-chloro-4-Y-amino-5-amino-pyrimidine (III), which compound is then cyclized to produce a 7-chloro-5-Q-3Y-3H-γ-triazolo [4,5-d]-pyrimidine. To obtain 7X-5Q-3Y-3H-γ-triazolo [4,5-d]-pyrimidines of formula I having a substituent other than a halogeno in the 7-position, simple replacement reactions may be effected.

In effecting the preparation of the 6-chloro-2-Q-4Y-amino-5-amino pyrimidines, 5-amino-2Q-4,6-dichloropyrimidine and the appropriate Y-amine (e.g. cyclohexylamine) is heated in an alkanol, preferably absolute ethanol, at a temperature range of about 80°–150° C, preferably 130°–135° C, in the presence of an efficient hydrochloric acid scavenger (e.g. triethylamine) or else an excess amount of the Y-amine may be utilized. The cyclization reaction may be effected at room temperature by admixing the reactants in an inert organic solvent in the presence of nitrous acid, per se, or a nitrite which will serve as a source of nitrous acid. Suitable nitrites are sodium nitrite and such organic nitrites as isoamyl nitrite, n-butyl nitrite and the like. Utilized as a diluent, in the presence of a suitable acid catalyst, such as aqueous acetic acid, ethanesulfonic acid, toluenesulfonic acid, hydrochloric acid and the like.

The foregoing reactions may be represented by the following generic reaction scheme:

REACTION SCHEME A

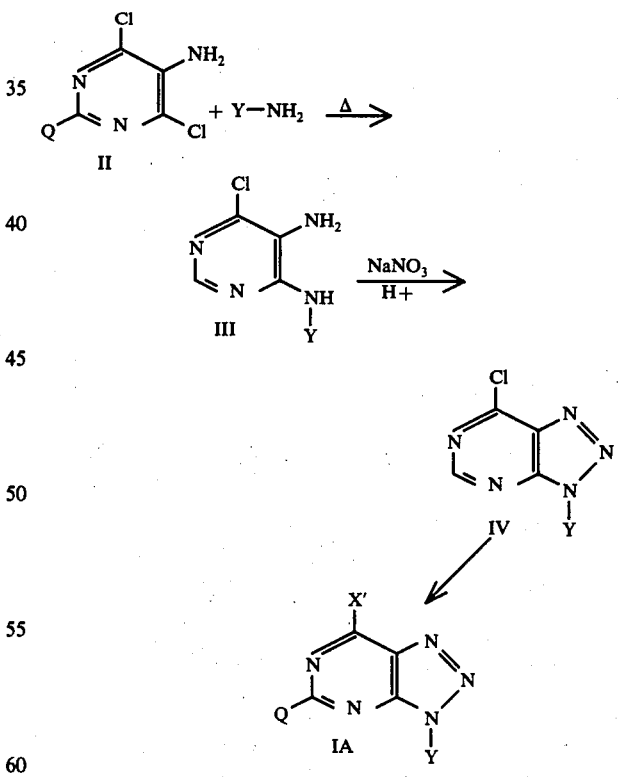

wherein Y and Q are as previously defined and X' represents a radical as defined for X except that it would not include chloro.

The preparation of the desired 5-amino-4,6-dichloropyrimidine may be effected by means well known in the art which, for the sake of brevity are depicted by the following reaction scheme:

REACTION SCHEME B

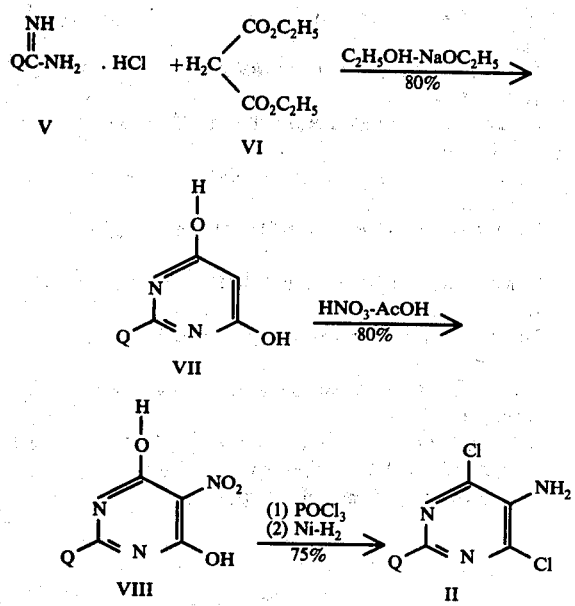

The following examples are used to illustrate the preparation of the compounds of this invention.

EXAMPLE 1

7-Chloro-3-Cyclohexyl 3H-γ-triazolo[4,5-d]-Pyrimidine

A. 5-Amino-4-Chloro-6-[N-(Cyclohexylamino)]-Pyrimidine:

Heat a solution of 5-amino-4,6-dichloropyrimidine (7 g.) and cyclohexylamine (22 g.) in absolute ethanol (60 ml.) in an autoclave at 130°–135° C for 6 hours. Cool the reaction vessel to room temperature and remove the solvents under reduced pressure. Partition the so-obtained residue between chloroform and water to remove cyclohexylamine hydrochloride. Dry the chloroform phase over anhydrous sodium sulfate and evaporate in vacuo to give a crystalline residue. Recrystallize the residue from methylene chloride-n-hexane to provide, as colorless crystals, 5-amino-4-chlor-6-[N-(cyclohexylamino)]pyrimidine; m.p. 134°–136° C.

B. 7-Chloro-3-Cyclohexyl 3H-γ-triazolo [4,5-d]-Pyrimidine

Suspend the pyrimidine (4 g.) from part A in 2N aqueous acetic acid (60 ml.) and cool the mixture to −5° C. With vigorous stirring add a 5% aqueous sodium nitrite solution (80 ml.) over 30 minutes. Stir the resulting mixture for an additional hour at −5° C, allow the mixture to warm to room temperature, filter and water-wash the white crystalline precipitate. Dissolve the precipitate in methylene chloride, dry over sodium sulfate, filter and recrystallize the desired 5-amino-4-chloro-6-[N-(cyclohexylamino)]-pyrimidine from methylenechloride-n-hexane; m.p. 74°–75° C.

In a similar manner, by substituting cyclohexylamine with an appropriate amine and by following substantially the same procedure of this example there is produced:

7-chloro-3-methyl-3H-γ-triazolo[4,5-d]-pyrimidine,
7-chloro-3,5-dimethyl-3H-γ-triazolo[4,5-d]-pyrimidine,
7-chloro-3-ethyl-3H-γ-triazolo[4,5-d]-pyrimidine,
7-chloro-3-butyl-3H-γ-triazolo[4,5-d]-pyrimidine,
7-chloro-3-(exo-2-norbonyl)-3H-γ-triazolo[4,5-d]-pyrimidine,
7-chloro-3-phenyl-3H-γ-triazolo[4,5-d]-pyrimidine,
7-chloro-3-p-chlorophenyl-3H-γ-triazolo[4,5-d]-pyrimidine,
7-chloro-3-cyclopentyl-3H-γ-triazolo[4,5-d]-pyrimidine,
7-chloro-3,5-di-cyclohexyl-3H-γ-triazolo[4,5-d]-pyrimidine,
7-chloro-3-cyclobutyl-5-cyclohexyl-3H-γ-triazolo[4,5-d]-pyrimidine,
7-chloro-3-isoamyl-3H-γ-triazolo[4,5-d]-pyrimidine,
7-chloro-3-cycloheptyl-3H-γ-triazolo[4,5-d]-pyrimidine,
7-chloro-3-benzyl-3H-γ-triazolo[4,5-d]-pyrimidine,
7-chloro-3-p-trifluoromethylbenzyl-3H-γ-triazolo[4,5-d]-pyrimidine,
7-chloro-3-(cis-myrtanyl)-5-cyclobutyl-3H-γ-triazolo[4,5-d]-pyrimidine,
7-chloro-3-phenethyl-3H-γ-triazolo[4,5-d]-pyrimidine,
7-chloro-3-(cis-myrtanyl)-3H-γ-triazolo[4,5-d]-pyrimidine.

EXAMPLE 2

7-Iodo-3-Cyclohexyl-3H-γ-Triazolo[4,5-d]-Pyrimidine

A mixture of 7-chloro-3-cyclohexyl-3H-γ-triazolo[4,5-d]-pyrimidine (817 mgms.) and sodium iodide (3.4 g.) was refluxed in dry glyme (60 ml.) for three days. The mixture was filtered and evaporated to dryness in vacuo. The residue obtained was taken up in ethyl acetate and washed with water. The ethyl acetate layer was dried over sodium sulfate and evaporated to give a white solid. Preparative layer-chromatography of the product on two 2mm. thick 20 cm × 20 cm silica GF plates using 15% acetone in n-hexane (4 elutions) as eluent, gave two fractions. The less polar fractions was unreacted starting compound, the more polar fraction was the desired 6-iodo compound containing 6-chloro compound as a minor impurity. The more polar fraction was rechromatographed as above to give the pure 7-iodo-3-cyclohexyl-3H-γ-triazolo[4,5-d]-pyrimidine which was crystallized from acetone-n-hexane, m.p. 108°–110° C.

In a similar manner by substituting the 7-chloro-3-cyclohexyl-3H-γ-triazolo[4,5-d]-pyrimidine with the appropriate 7-chloro-3Y-3H-γ-triazolo[4,5-d]-pyrimidine and by substantially following the procedure of the foregoing example there is produced:

7-iodo-3-methyl-3H-γ-triazolo[4,5-d]-pyrimidine,
7-iodo-3-ethyl-3H-γ-triazolo[4,5-d]-pyrimidine,
7-iodo-3-butyl-3H-γ-triazolo[4,5-d]-pyrimidine,
7-iodo-3-(exo-2-norbonyl)-3H-γ-triazolo[4,5-d]-pyrimidine,
7-iodo-3-phenyl-3H-γ-triazolo[4,5-d]-pyrimidine,
7-iodo-3-p-chlorphenyl-3H-γ-triazolo[4,5-d]-pyrimidine,
7-iodo-3-cyclopentyl-3H-γ-triazolo[4,5-d]-pyrimidine,
7-iodo-3-isoamyl-3H-γ-triazolo[4,5-d]-pyrimidine,
7-iodo-3-cycloheptyl-3H-γ-triazolo[4,5-d]-pyrimidine,
7-iodo-3-benzyl-3H-γ-triazolo[4,5-d]-pyrimidine, 7-iodo-3-p-trifluoromethylbenzyl-3H-γ-triazolo[4,5-d]-pyrimidine, 7-iodo-3-phenethyl-3H-γ-triazolo[4,5-d]-pyrimidine.

EXAMPLE 3

7-N-Dimethylamino-3-Cyclopentyl-3H-γ-triazolo[4,5-d]-Pyrimidine

A solution of 7-chloro-3-cyclopentyl-3H-γ-triazolo[4,5-d]-pyrimidine (900 mgs.) in tetrahydrofuran (15 ml.) was treated with dimethylamine (1 ml.) and the mixture refluxed for 3 hours. After cooling to room temperature, solvents were removed in vacuo and the residue taken up in chloroform. The chloroform solution was washed with water, dried, charcoalized and filtered. After removal of the solvent the remaining residue was crystallized to yield 7-N-dimethylamino-3-cyclopentyl-3H-γ-triazolo[4,5-d]-pyrimidine.

By substitution of the 3H-γ-triazolo[4,5-d]-pyrimidine reactant of this reaction and by following substantially the same procedure of this example, there is produced:

7-N-dimethylamino-3-methyl-3H-γ-triazolo[4,5-d]-pyrimidine,

7-N-dimethylamino-3-ethyl-3H-γ-triazolo[4,5-d]-pyrimidine,

7-N-dimethylamino-3-butyl-3H-γ-triazolo[4,5-d]-pyrimidine,

7-N-dimethylamino-3-adamantyl-3H-γ-triazolo[4,5-d]-pyrimidine,

7-N-dimethylamino-3-phenyl-3H-γ-triazolo[4,5-d]-pyrimidine,

7-N-dimethylamino-3-p-chlorophenyl-3H-γ-triazolo[4,5-d]-pyrimidine,

7-N-dimethylamino-3-isoamyl-3H-γ-triazolo[4,5-d]-pyrimidine,

7-N-dimethylamino-3-cycloheptyl-3H-γ-triazolo[4,5-d]-pyrimidine,

7-N-dimethylamino-3-benzyl-3H-γ-triazolo[4,5-d]-pyrimidine,

7-N-dimethylamino-3-phenethyl-3H-γ-triazolo[4,5-d]-pyrimidine.

EXAMPLE 4

7-Diethylamino-3-(exo-2-norbonyl)-3H-γ-Triazolo[4,5-d]-Pyrimidine

7-Chloro-3-(exo-2-norbonyl)-3H-γ-triazolo[4,5-d]-pyrimidine (110 mgs.) was suspended in methanol (5 ml.) and treated with diethylamine (0.1 ml.). The mixture was stirred for approximately 100 hours. The product (97 mgs.) separated as a colorless crystalline solid.

By substitution of the 3H-γ-triazolo[4,5-d]-pyrimidine reactant of this reaction and by following substantially the same procedure of this example, there is produced:

7-diethylamino-3-methyl-3H-γ-triazolo[4,5-d]-pyrimidine, 7-diethylamino-3-ethyl-3H-γ-triazolo[4,5-d]-pyrimidine, 7-diethylamino-3-butyl-3H-γ-triazolo[4,5-d]-pyrimidine, 7-diethylamino-3-(cis-myrtanyl)-3H-γ-triazolo[4,5-d]-pyrimidine, 7-diethylamino-3-(trans-myrtanyl)-3H-γ-triazolo[4,5-d]-pyrimidine, 7-diethylamino-3-p-chlorophenyl-3H-γ-triazolo[4,5-d]-pyrimidine, 7-diethylamino-3-isoamyl-3H-γ-triazolo[4,5-d]-pyrimidine, 7-diethylamino-3-cycloheptyl-3H-γ-triazolo[4,5-d]-pyrimidine, 7-diethylamino-3-benzyl-3H-γ-triazolo-[4,5-d]-pyrimidine, 7-diethylamino-3-phenethyl-3H-γ-triazolo-[4,5-d]-pyrimidine.

Although most of the compounds of formula I are known compounds, the following sub-genus represents a cohesive group of novel compounds:

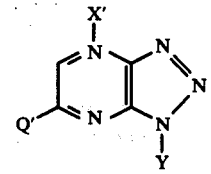

wherein X' is halogeno, Y is selected from the group consisting of lower alkyl, cycloalkyl, hydroxy cycloalkyl, phenyl, bicycloalkyl, or A—$R_2$ with A being methylene or ethylene and $R_2$ being phenyl or bicycloalkyl, and Q' is as defined for Y.

We claim:

1. A compound selected from the group consisting of 7-chloro-3-cyclohexyl-3H-γ-triazolo[4,5-d]-pyrimidine, 7-chloro-3-cycloheptyl-3H-γ-triazolo[4,5-d]-pyrimidine, 7-chloro-3-cyclobutyl-3H-γ-triazolo[4,5-d]-pyrimidine, 7-iodo-3-cyclohexyl-3H-γ-triazolo[4,5-d]-pyrimidine, and 7-methoxy-3-cyclopentyl-3H-γ-triazolo[4,5-d]-pyrimidine.

2. A compound of claim 1, said compound being 7-chloro-3-cyclohexyl-3H-γ-triazolo[4,5-d]-pyrimidine.

3. A compound of claim 1, said compound being 7-chloro-3-cycloheptyl-3H-γ-triazolo[4,5-d]-pyrimidine.

4. A compound of claim 1, said compound being 7-chloro-3-cyclobutyl-3H-γ-triazolo[4,5-d]-pyrimidine.

5. A compound of claim 1, said compound being 7-iodo-3-cyclohexyl-3H-γ-triazolo[4,5-d]-pyrimidine.

6. A compound of claim 1, said compound being 7-methoxy-3-cyclopentyl-3H-γ-triazolo[4,5-d]-pyrimidine.

* * * * *